United States Patent
Takahashi et al.

(10) Patent No.: US 12,116,329 B2
(45) Date of Patent: Oct. 15, 2024

(54) METHOD FOR PRODUCING DIFLUOROETHYLENE

(71) Applicant: DAIKIN INDUSTRIES, LTD., Osaka (JP)

(72) Inventors: Kazuhiro Takahashi, Osaka (JP); Osamu Yamamoto, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 333 days.

(21) Appl. No.: 17/544,053

(22) Filed: Dec. 7, 2021

(65) Prior Publication Data

US 2022/0089512 A1    Mar. 24, 2022

Related U.S. Application Data

(63) Continuation of application No. PCT/JP2020/022770, filed on Jun. 10, 2020.

(30) Foreign Application Priority Data

Jun. 10, 2019 (JP) .................. 2019-107970

(51) Int. Cl.
*C07C 17/358* (2006.01)
*C07C 17/383* (2006.01)

(52) U.S. Cl.
CPC .......... *C07C 17/358* (2013.01); *C07C 17/383* (2013.01)

(58) Field of Classification Search
CPC .................................................. C07C 17/358
See application file for complete search history.

(56) References Cited

U.S. PATENT DOCUMENTS

2021/0246090 A1    8/2021    Usui et al.

FOREIGN PATENT DOCUMENTS

| JP | 2015-229768 | 12/2015 |
| JP | 2019-214535 | 12/2019 |

OTHER PUBLICATIONS

International Search Report issued Sep. 8, 2020 in International (PCT) Application No. PCT/JP2020/022770.
Wampler, F.B., "The $SO_2(^3B_1)$ Photosensitized Isomerization of Cis- and Trans-1, 2-Difluoroethylene", International Journal of Chemical Kinetics, 1976, vol. 8, pp. 511-517.
Wampler, F.B.' "The Photolysis of $SO_2$ at 3080 Å in the Presence of Cis- and Trans-1, 2-Difluoroethylene", International Journal of Chemical Kinetics, 1976, vol. 8, pp. 519-528.
Strausz, O.P. et al., "Mercury $6(^3P1)$ Photosensitization of Mono- and Difluoroethylenes. Correlation of Mechanism with Calculated Molecular Orbital Energy Levels", Journal of the American Chemical Society, 1970, vol. 92, No. 22, pp. 6395-6402.
(Continued)

*Primary Examiner* — Medhanit W Bahta
(74) *Attorney, Agent, or Firm* — Wenderoth, Lind & Ponack, L.L.P.

(57) ABSTRACT

Provided is a method for efficiently obtaining HFO-1132(E) and/or HFO-1132(Z). The method includes supplying a composition containing HFO-1132(E) and/or HFO-1132(Z) to a reactor to perform isomerization between HFO-1132(E) and HFO-1132(Z) by irradiating the composition with light.

3 Claims, 1 Drawing Sheet

Method for Producing HFO-1132(E) and/or HFO-1132(Z)

Starting Material: Composition Containing HFO-1132(E) and/or HFO-1132(Z)

(56) References Cited

OTHER PUBLICATIONS

Guillory, W. A. et al., "The vacuum-ultraviolet photolysis of the difluoroethylenes", The Journal of Chemical Physics, 1975, vol. 62, No. 8, pp. 3208-3216.
Craig, N. C. et al., "Thermodynamics of cis-trans isomerizations. The 1,2-difluoroethylenes", Journal of the American Chemical Society, 1961, vol. 83, pp. 3047-3050.
English language translation of International Preliminary Report on Patentability issued Dec. 14, 2021 in corresponding International (PCT) Patent Application No. PCT/JP2020/022770.
Extended European Search Report issued Jun. 21, 2023 in corresponding European Patent Application No. 20822393.3.
F.D. Gunstone, Guidebook to Stereochemistry, Section "2.9 Interconversion of cis and trans isomers," Chemical Industry Press, 1982 (Beijing First Edition), p. 18, with English translation.
Lin Xu et al., Theoretical Organic Chemistry, "Chapter V Stereochemistry", China Science and Technology Press, 2006, pp. 119-121, with English translation.

Method for Producing HFO-1132(E) and/or HFO-1132(Z)

Starting Material:
Composition Containing HFO-1132(E) and/or HFO-1132(Z)

For Efficiently Producing HFO-1132(E) (Trans Form)

Starting Material:
Composition Containing HFO-1132(E) and/or HFO-1132(Z)

METHOD FOR PRODUCING DIFLUOROETHYLENE

TECHNICAL FIELD

The present disclosure relates to a method for producing difluoroethylene.

BACKGROUND ART

Non-patent Literature (NPL) 1 discloses a method for isomerizing HFO-1132(Z) into HFO-1132(E) by bringing iodine (catalyst) into contact with HFO-1132(Z) in a gas phase.

CITATION LIST

Non-patent Literature

NPL 1: Journal of the American Chemical Society, 1961, vol. 83, 3047

SUMMARY

Item 1.

A method for producing HFO-1132(E) and/or HFO-1132 (Z), comprising supplying a composition containing trans-1,2-difluoroethylene (HFO-1132(E)) and/or cis-1,2-difluoroethylene (HFO-1132(Z)) to a reactor to perform isomerization between HFO-1132(E) and HFO-1132(Z) by irradiating the composition with light having a wavelength of 10 nm or more and 400 nm or less.

Advantageous Effects of Invention

The present disclosure enables the efficient production of HFO-1132(E) and/or HFO-1132(Z).

DESCRIPTION OF EMBODIMENTS

The present inventors found that because the conventional method for obtaining HFO-1132 by performing dehydrofluorination on a trihalogenated ethane such as 1,1,2-trifluoroethane (HFC-143) (starting material) in the presence of a catalyst produces HFO-1132(E) and HFO-1132(Z) (isomers) together, the method is inefficient from a cost perspective when only one isomer is desired while the other is unnecessary, and that due to the use of iodine, which is highly corrosive and has a low sublimation point, it is difficult to organize equipment for conventional isomerization.

Accordingly, an object of the present disclosure is to provide a means for solving the problems. Specifically, an object of the disclosure is to provide a method for more efficiently obtaining HFO-1132(E) and/or HFO-1132(Z) when HFO-1132(E) and HFO-1132(Z) are produced together, such as in a method for obtaining HFO-1132 by using the dehydrohalogenation of trihalogenated ethane.

The present inventors conducted extensive research to solve the problems and found that the isomerization of a reaction composition containing HFO-1132 obtained by dehydrohalogenation of trihalogenated ethane is possible by performing light irradiation. The inventors also found that the combination of the step of performing isomerization and the step of separating a desired isomer can solve the problems. The present disclosure was completed by further conducting research on the basis of these findings, and includes the following aspects.

1. Step of Performing Isomerization

Figure 1:
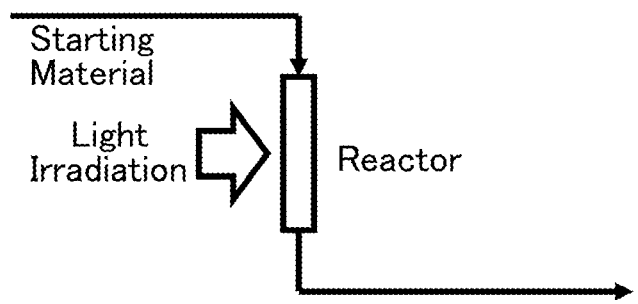
FIG. 1 is a drawing schematically showing the method for producing HFO-1132(E) and/or HFO-1132(Z) according to the present disclosure.

The production method according to the present disclosure is a method for producing HFO-1132(E) and/or HFO-1132(Z), comprising supplying a composition containing HFO-1132(E) and/or HFO-1132(Z) to a reactor to perform isomerization between HFO-1132(E) and HFO-1132(Z) by irradiating the composition with light having a wavelength of 10 nm or more and 400 nm or less (light irradiation) (FIG. 1).

The production method according to the present disclosure is a method for producing HFO-1132(E), comprising supplying HFO-1132(Z), or a composition containing HFO-1132(E) and HFO-1132(Z), to a reactor to perform isomerization between HFO-1132(E) and HFO-1132 (Z) by irradiating HFO-1132(Z) or the composition with light having a wavelength of 10 nm or more and 400 nm or less (light irradiation).

The present disclosure includes performing isomerization between HFO-1132(Z) and HFO-1132(Z). This isomerization follows the reaction scheme described below. Because the F-isomer is thermodynamically less stable than the Z-isomer, this equilibrium is biased to the Z-isomer.

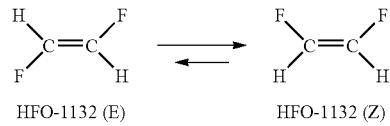

HFO-1132 (E)          HFO-1132 (Z)

In the present disclosure, a composition containing HFO-1132(E) and/or HFO-1132(Z) is subjected to isomerization, thereby obtaining a composition in which the content of HFO-1132(E) is increased. Performing light irradiation and isomerization decreases the content of HFO-1132(Z), while increasing the content of HFO-1132(E).

In the present disclosure, the isomerization is preferably performed in a gas phase.

In the present disclosure, the light irradiation in isomerization is preferably performed by irradiation with light having a wavelength of 10 nm or more and 400 nm or less.

In the present disclosure, the use of equilibrium relation in the isomerization between HFO-1132(E) and HFO-1132 (Z) provides a composition in which the content of either compound is increased.

1-1. Composition Containing HFO-1132(E) and/or HFO-1132(Z)

The composition containing HFO-1132(E) and/or HFO-1132(Z) for use as a starting material of the isomerization may contain other components. The other components can be any component that does not greatly interfere with the isomerization, and can be selected from a wide range.

Examples of such other components include impurities incorporated during the process of obtaining the composition containing HFO-1132(E) and/or HFO-1132(Z), and generated by-products. The incorporated impurities include impurities contained in the starting material.

An example of the method for obtaining a composition containing HFO-1132(E) and/or HFO-1132(Z) (starting material) is a method of subjecting halogenated ethane to dehydrohalogenation or dehalogenation. The halogenated ethane for use in this reaction can be any halogenated ethane, and can be selected from a wide range. Specific examples include the following halogenated ethane. These kinds of halogenated ethane are widely used, for example, in refrigerants, solvents, foaming agents, or propellants, and are readily available.

1,1,2-trifluoroethane ($CHF_2CH_2F$, HFC-143)
1-bromo-1,2-difluoroethane ($CHFBrCH_2F$)
1-chloro-1,2-difluoroethane ($CHClFCH_2F$)
1,2-dichloro-1,2-difluoroethane ($CHClFCHlF$)
1,1,2,2-tetrafluoroethane ($CHF_2CHF_2$)
1-chloro-1,2,2-trifluoroethane ($CHClFCHF_2$)

In the present disclosure, in particular, in the method for producing HFO-1132(E), the use of HFO-1132(Z) as a starting material allows the isomerization of HFO-1132(Z) into HFO-1132(E) to effectively proceed.

1-2. Reaction Conditions

Temperature, Time, and Pressure in Reaction

The reaction temperature for isomerization in the present disclosure is not limited and can be suitably set. The reaction temperature can be within the range of about −20° C. to 200° C., and preferably about 0° C. to 100° C.

The reaction time for isomerization in the present disclosure is not limited and can be suitably set. The longer the contact time, the more the conversion rate is increased. However, because a longer light irradiation time is inefficient, an appropriate residence time can be set. The reaction time is typically set within the range of about 0.1 seconds to 100 seconds, and preferably about 1 second to 50 seconds.

The pressure of the reactor for isomerization in the present disclosure is not limited and can be suitably set. Because a higher pressure promotes the formation of polymerized materials such as tar, an appropriate pressure can be set for isomerization in the present disclosure. The pressure of the reactor is typically within the range of about atmospheric pressure to 0.2 MPa, and preferably about atmospheric pressure to 0.1 MPa. In the present disclosure, the pressure is gauge pressure unless indicated otherwise.

Gas Phase Reaction

In the present disclosure, isomerization is preferably performed in a gas phase. Isomerization is preferably performed in the presence of a diluted gas. The diluted gas for use may be a gas such as oxygen, $N_2$ gas, helium gas, HF gas, and argon gas, and is particularly preferably $N_2$ gas from a cost perspective.

To perform isomerization in the presence of a diluted gas, a diluted gas can be supplied to a reactor. The amount of the diluted gas to be supplied can be suitably set. In particular, the diluted gas is preferably supplied such that the molar ratio of the amount of the diluted gas to the total amount of HFO-1132(E) and HFO-1132(Z) is 0.01 to 3.0, more preferably 0.1 to 2.0, and still more preferably 0.2 to 1.0.

Light Irradiation

The light irradiation for isomerization in the present disclosure is performed by irradiation of light with a wavelength of 10 nm or more and 400 nm or less. The light source for use in performing light irradiation is preferably, although not limited to, an excimer lamp, a low-pressure mercury lamp, a deuterium lamp, or a like lamp.

In the present disclosure, the light irradiation device for use may be, for example, a batch-mode excimer irradiation device (Model: MECL01U-1). For example, light irradiation can be performed with the number of lamps set to one, and the light irradiation area set to an effective length of about 140 mm×10 to 30 mm. In the present disclosure, light irradiation can be performed with light having a wavelength of 172 nm and an illuminance of 80 mW/cm$^2$ or more. The reaction tube for use in light irradiation is preferably a synthetic quartz tube with a diameter of 3 mm and a length of 150 mm (F310, produced by Shin-Etsu Quartz Products Co., Ltd.) because light irradiation is suitably performed at a wavelength of 172 nm.

A feature of the production method according to the present disclosure is to perform light irradiation by directly irradiating the molecules of HFO-1132(E) and/or HFO-1132(Z) to allow isomerization to proceed due to the use of light having a wavelength of 10 nm or more and 400 nm or less. Not requiring a photosensitizer or a catalyst as essential components, the production method according to the present disclosure is an economically advantageous method for producing HFO-1132(E) and/or HFO-1132(Z).

Reaction in Batch Mode

In the present disclosure, isomerization is preferably performed in a gas phase, and isomerization is preferably performed by using a reactor of batch mode. In the reaction in batch mode, a reactor with a closed reaction system can be used.

When the reaction is performed in batch mode, it is preferred that, for example, the reactor is filled with a composition containing HFC-1132(E) and/or HFO-1132(Z), which is a starting material for isomerization, and that light irradiation is performed at a reaction temperature suitably adjusted by using a heater or other equipment to allow a reaction to proceed for a predetermined period of time. The reaction atmosphere in which the reaction is performed is preferably an atmosphere of inert gas such as nitrogen, helium, or carbon dioxide.

In the present disclosure, when the isomerization is performed in batch mode (e.g., a closed reaction system), the reaction temperature is preferably within the range of about −20° C. to 200° C., and more preferably about 0° C. to 100° C., from the standpoint of more efficiently performing isomerization.

In the present disclosure, performing isomerization with a batch-mode reactor (e.g., sealed reactor) efficiently produces HFO-1132(E) and/or HFO-1132(Z).

Reaction by Flow Process

In the present disclosure, isomerization is preferably performed in a gas phase, and isomerization is preferably performed by a gas-phase continuous-flow process by using a fixed-bed reactor for performing isomerization. Performing isomerization by a gas-phase continuous-flow process simplifies the equipment and operation, and is thus economically advantageous. When the reaction is performed in flow mode, it is preferred that, for example, the reactor is filled with a composition containing HFO-1132(E) and/or HFO-1132(Z), which is a starting material for isomerization, and that light irradiation is performed at a reaction temperature suitably adjusted by using a heater to allow a reaction to proceed for a predetermined period of time. The reaction atmosphere in which the reaction is performed is preferably an atmosphere of inert gas such as nitrogen, helium, or carbon dioxide.

In the present disclosure, when isomerization is performed by a reaction in flow mode (e.g., gas-phase continuous-flow process), the reaction temperature is preferably within the range of about −20° C. to 200° C., and more preferably about 0° C. to 100° C., from the standpoint of allowing isomerization to more efficiently proceed.

In the step of isomerization in the present disclosure, HFO-1132(E) and/or HFO-1132(Z) can be efficiently obtained by performing isomerization in a reactor for flow mode (e.g., a gas-phase continuous-flow reactor).

The isomerization can be performed either in flow mode, which continuously supplies a starting material to the reactor and continuously extracts the target compound from the reactor, or in batch mode. The isomerization is preferably performed in flow mode because the target compound does not remain in the reactor, and isomerization continuously proceeds.

2. Separation Step

Figure 2:
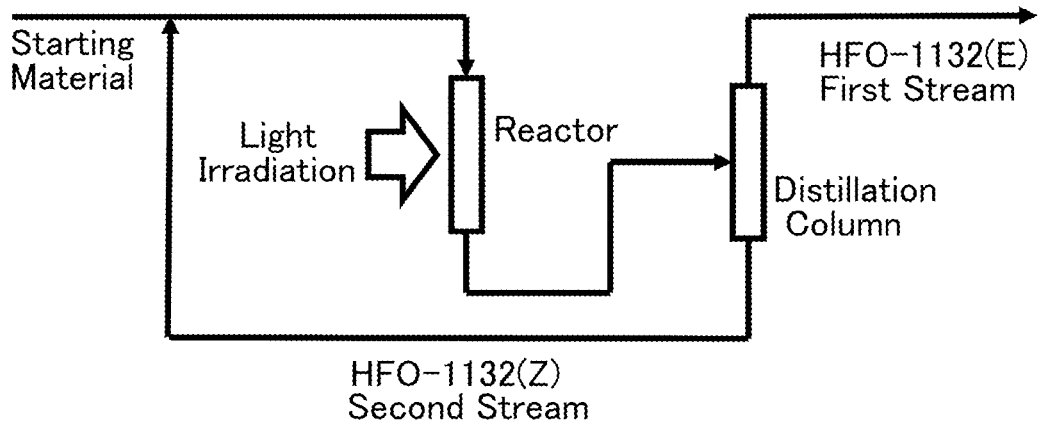
FIG. 2 is a drawing schematically showing the method for efficiently obtaining HFO-1132(E) in the method for producing HFO-1132(E) and/or HFO-1132(Z) according to the present disclosure.

The present disclosure includes, after the isomerization, separating HFO-1132(E) and HFO-1132(Z) by distillation to produce HFO-1132(E) and/or HFO-1132(Z) (FIG. 2).

Because HFO-1132(E) has a boiling point of −53° C., and HFO-1132(Z) has a boiling point of −26° C., HFC-1132(E) and HFO-1132(Z) are separated by distillation by using the difference in their boiling points.

The reaction product obtained in the isomerization is separated, for example, into the first stream, mainly composed of HFO-1132(E), and the second stream, mainly composed of HFO-1132(Z). Specifically, the gas produced by the isomerization present in the reactor outlet is cooled to be liquefied and then distilled to be separated into the first stream, mainly composed of HFO-1132(E), and the second stream, mainly composed of HFO-1132(Z).

3. Recycling Step

The present disclosure preferably includes, after the separation, transferring HFO-1132(Z) to the reactor for recycling and subjecting HFO-1132(Z) to isomerization again to produce EEC-1132 (E) and/or HFO-1132 (Z) (FIG. 2).

In the present disclosure, the first stream, mainly composed of HFO-1132(E), or the second stream, mainly composed of HFO-1132(Z), obtained by the separation step can be recycled in the isomerization in order to collect a composition with a higher content of either HFO-1132(E) or HFO-1132(Z).

After the separation, for example, recycling the second stream, mainly composed of HFO-1132(Z), provides a composition in which the content of HFO-1132(E) has been increased by isomerization after recycling. Recycling the first stream, mainly composed of HFO-1132(E), in the recycling step and performing isomerization after recycling provide a composition in which the content of HFO-1132(Z) has been increased.

The production method according to the present disclosure makes it possible to convert an undesired isomer, which is unavoidable byproduct generated during the production of HFO-1132(E) and/or HFO-1132(Z), into a desired isomer highly efficiently, thus greatly improving the economic performance of the method for producing the desired isomer. The HFO-1132(E) and/or HFO-1132(Z) produced by the production method according to the present disclosure can be effectively used in various areas, such as for raw materials for resin products, organic synthetic intermediates, and heat media.

Item 1.

A method for producing HFO-1132 (E) and/or HFO-1132 (Z), comprising supplying a composition containing trans-1,2-difluoroethylene (HFO-1132(E)) and/or cis-1,2-difluoroethylene (HFO-1132(Z)) to a reactor to perform isomerization between HFO-1132(E) and HFO-1132(Z) by irradiating the composition with light having a wavelength of 10 nm or more and 400 nm or less.

Item 2.

A method for producing HFO-1132(E), comprising supplying HFO-1132(Z), or a composition containing HFO-1132(E) and HFO-1132(Z), to a reactor to perform isomerization between HFO-1132(E) and HFO-1132(Z) by irradiating HFO-1132(Z) or the composition with light having a wavelength of 10 nm or more and 400 nm or less.

Item 3.

The method according to Item 1 or 2, wherein the isomerization is performed in a gas phase.

Item 4.

The method according to any one of Items 1 to 3, comprising, after the isomerization, separating HFO-1132 (E) and HFO-1132(Z) by distillation.

Item 5.

The method according to Item 4, comprising, after the separation, recycling HFO-1132(Z) in the isomerization to subject HFO-1132(Z) to isomerization again.

EXAMPLES

The following describes the present disclosure with reference to Examples. However, the disclosure is not limited to these Examples.

(1) Isomerization

A composition containing HFO-1132(E) and/or HFO-1132(Z)(starting material composition) was supplied to a reactor, and isomerization between HFO-1132(E) and HFO-1132(Z) was performed by light irradiation, thereby obtaining a reaction composition in which the isomer concentration of HFO-1132(E) was higher than in the supplied starting material composition.

Isomerization Conditions

Light Irradiation Device: batch-mode excimer irradiation device (model: MECL01U-1)

Light Irradiation Area: effective length of about 140 mm×10 to 30 mm (172 nm)

Number of Lamps: 1

Wavelength and Illuminance: 172 nm, 80 mW/cm$^2$ or more

Reaction Tube: Shin-Etsu Quartz F310 (synthetic quartz tube, diameter: 3 mm×length 150 mm)

Residence Time: 60 seconds

Reaction Temperature: 30° C.

(2) Results of Isomerization

Table 1 shows the results of the reaction.

TABLE 1

| Light Irradiation | HFO-1132 (E) | HFO-1132 (Z) |
| --- | --- | --- |
| Before Irradiation | 0.11% | 99.89% |
| After Irradiation | 5.0% | 95.0% |

Evaluation confirmed that the production method according to the present disclosure can construct a method for efficiently producing the target HFO-1132(E) and/or HFO-1132(Z), and can produce, in particular, HFO-1132(E) highly efficiently.

The invention claimed is:

1. A method for producing HFO-1132(E), comprising:
supplying HFO-1132(Z), or a composition containing HFO-1132(E) and HFO-1132(Z), to a reactor to perform isomerization between HFO-1132(E) and HFO-1132(Z) by irradiating HFO-1132(Z) or the composition with light having a wavelength of 10 nm or more and 172 nm or less, wherein a reaction time for the isomerization is set within a range of 0.1 seconds to 100 seconds, and the isomerization is performed in a gas phase.

2. The method according to claim 1, comprising, after the isomerization,
where HFO-1132(Z) is contained in the reaction product obtained in the isomerization, separating the HFO-1132(E) and the HFO-1132(Z) by distillation.

3. The method according to claim 2, comprising, after the separation,
recycling the HFO-1132(Z) in the isomerization to subject the HFO-1132(Z) to isomerization again, thereby providing a composition in which a content of HFO-1132(E) is increased by the isomerization after recycling.

* * * * *